(12) United States Patent
Meyer et al.

(10) Patent No.: US 7,097,828 B2
(45) Date of Patent: Aug. 29, 2006

(54) SUNSCREEN FORMULATIONS CONTAINING WATERBORNE POLYURETHANE POLYMERS

(75) Inventors: Thomas A. Meyer, Germantown, NJ (US); Donathan G. Beasley, Memphis, TN (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 408 days.

(21) Appl. No.: 10/185,070

(22) Filed: Jun. 28, 2002

(65) Prior Publication Data

US 2003/0044364 A1 Mar. 6, 2003

Related U.S. Application Data

(60) Provisional application No. 60/302,056, filed on Jun. 29, 2001.

(51) Int. Cl.
*A61K 7/42* (2006.01)
*A61K 7/44* (2006.01)
*A61K 31/74* (2006.01)
*A61K 7/00* (2006.01)

(52) U.S. Cl. .................. 424/59; 424/60; 424/78.02; 424/78.08; 424/400; 424/401

(58) Field of Classification Search .............. 424/59, 424/60, 78.02, 78.08, 400, 401
See application file for complete search history.

(56) References Cited

U.S. PATENT DOCUMENTS

| 5,188,831 A | * | 2/1993 | Nicoll et al. ............. 424/401 |
| 6,017,997 A | | 1/2000 | Snow |
| 6,491,932 B1 | * | 12/2002 | Ramin et al. ............ 424/401 |

OTHER PUBLICATIONS

Brochure, B.F. Goodrich, Avalure Film Forming Polymers For Personal Care Applications.

* cited by examiner

*Primary Examiner*—Shelley A. Dodson

(57) ABSTRACT

A formulation for topical application, the formulation comprising a waterborne polyurethane polymer; a thickening agent; a humectant, at least one sunscreen active agent, and an emulsifying agent.

21 Claims, No Drawings

SUNSCREEN FORMULATIONS CONTAINING WATERBORNE POLYURETHANE POLYMERS

This application claims formal benefit of priority to Provisional U.S. Patent Application Ser. No. 60/302,056, filed Jun. 29, 2001.

BACKGROUND OF THE INVENTION

The invention relates to formulations that are applied to the skin to reduce the amount of solar ultraviolet radiation received by the skin. More particularly, the invention relates to formulations containing waterborne polyurethane polymers that impart several beneficial properties to topical formulations, including inter alia, water proofing, reduction in the migration of the formulation across the wearer's skin, and reduction of the penetration of the active ingredients of the formulation into the wearer's stratum corneum.

It is now generally recognized that exposure to solar radiation can have adverse health consequences, sometimes not appearing until several years following the exposure. Of course, the immediately appearing sunburn from an overexposure can itself be a serious acute health problem.

Many products are available to reduce the amount of solar ultraviolet radiation received by the skin during exposure to the sun's rays. Typical product formulations are lotions, creams, ointments or gels containing chemical and/or physical barriers to ultraviolet transmission. These vary considerably in their abilities to protect the skin against the physical and biochemical effects of ultraviolet radiation. Many conventional cosmetic cream and lotion compositions are described, for example, in Sagarin, Cosmetics Science and Technology, 2nd Edition, Volume 1, Wiley Interscience (1972), and Encyclopedia of Chemical Technology, Third Edition, Volume 7.

Earlier sunscreening formulations were designed to protect against sunburn from a limited solar exposure period, while transmitting sufficient radiation to permit skin tanning. However, the current focus is on eliminating as much ultraviolet radiation exposure as possible, it being recognized that skin tanning, while esthetically pleasing to some, is a clear indication of tissue damage from overexposure to solar radiation. It has been recently discovered that any amount of unprotected exposure can potentially cause immune system suppression and lead to future health problems, such as skin carcinomas and other dermatological disorders.

The SPF (Sun Protection Factor) rating system has been developed to provide consumer guidance in selecting suitable sunscreens for any given outdoor activity. In general, the SPF number approximately corresponds to the multiple of time during which the properly applied sunscreen will prevent obvious reddening of the skin, over the exposure time that causes unprotected skin to exhibit reddening. Thus, if an SPF 8 sunscreen formulation has been properly applied, a person should be able to remain in the sun without visible effects for eight times the usual unprotected duration. Of course, the duration of unprotected exposure which produces a visible effect on the skin varies from one individual to another, due to differences in their skin cells. Currently popular are high-SPF "sunblocker" products, having SPF values of at least 30.

Most of the commercially available sunscreen formulations are not well suited for use by those engaged in strenuous outdoor activities, such as construction work, gardening, athletic events and many others, due to the tendency for perspiration from the body to interact with the applied formulation. For example, perspiration, or moisture from other sources, including rain, can cause sunscreen active ingredients and other irritating components of the formulation to enter the eyes and cause discomfort. It is also frequently detrimental, particularly in activities such as tennis which require a reliable grip on equipment, to have an applied sunscreen formulation remain lubricious after application or become lubricious when mixed with perspiration or other moisture.

It is also advantageous to have a suncare formulation that is waterproof. Waterproof formulations allow the user to engage in activities such as swimming while still being protected against ultraviolet radiation. Hydrophobic materials typically serve as waterproofing agents that impart film forming and waterproofing characteristics to an emulsion. However, there is still a need for products having physical attributes that display improved waterproof performance, that have a reduction in migration of the formulation across the formulation wearer's skin, and have a reduction in the penetration of the active ingredients into the formulation wearer's skin.

A sunscreen product that has been available for several years, but which does not exhibit disadvantages such as the foregoing, is sold by Schering-Plough HealthCare Products, Inc., Memphis, Tenn. U.S.A. as COPPERTONE.RTM. SPORT.RTM. SPF 30 lotion. This product contains the active ingredients octyl salicylate, octyl methoxycinnamate and oxybenzone, totaling 17.5 weight percent of the formulation, and is an oil-in-water emulsion formulated with 1.5 weight percent of a fumed silica having a hydrophobic surface treatment. It is thought that the silica serves to immobilize the active agents in the internal phase of the formulation and inhibit their migration under the influence of skin oils and/or external moisture. The product also has a very desirable "dry" feel as it is being applied, quite unlike the very liquid nature of the usual lotion which does not contain particulate ingredients other than those approved for use as sunscreen active ingredients.

Not with standing the foregoing, there still exists a need for a waterproof formulation that exhibits beneficial properties such as a decreased partitioning of the formulation into the wearer's stratum corneum and a reduction in the migration of the sunscreen active agents across the wearers skin upon topical application of the formulation.

SUMMARY OF THE INVENTION

The present invention provides a sunscreen formulation for topical application, the formulation comprising a waterborne polyurethane polymer, a thickening agent, a humectant, an emulsifying agent, and at least one sunscreen active agent.

The invention also provides a sunscreen formulation comprising an oil-in-water emulsion formulation, the formulation comprising a nonaqueous phase, an aqueous phase, an oil in water emulsifying agent, a waterborne polyurethane polymer, a humectant, a thickening agent, and at least one sunscreen active agent.

The invention also provides a sunscreen formulation comprising an oil-in-water emulsion formulation, the formulation comprising an non-aqueous phase, an aqueous phase, an oil-in-water emulsifying agent, a water borne polyurethane polymer; a humectant, a thickening agent, at least one sunscreen active agent and at least one insect repellant active agent.

The inventive formulations of the present invention exhibit improved waterproof performance, a reduction in migration of sunscreen active agents across the skin's surface, and a retardation of penetration of the sunscreen active agents into the formulation wearer's skin.

DETAILED DESCRIPTION OF THE INVENTION

Names given to chemical substances herein generally are either accepted chemical names, or are trade organization or regulatory agency approved names such as CTFA Adopted Names as listed in J. A. Wenninger et al., Eds., CTFA International Cosmetic Ingredient Dictionary, Eighth Ed. and Tenth Ed., The Cosmetic, Toiletry and Fragrance Association, Washington, D.C., 1997 and 2000, respectively.

In this application, the term "percent" shall mean percent by weight unless the context clearly indicates otherwise.

The waterproofing agents of the present invention are linear, aliphatic waterborne polyurethane polymers. The preferred polyurethanes are available from BF Goodrich under the tradename of Avalure UR 445 and Avalure UR 450. Avalure UR 445 is identified as polyurethane 4 by the INCI and/or the CTFA. The polyurethane has a Brookfield viscosity of about 30–1000 cP, is about 40% solid, has a pH of about 7 to 9, and is substantially NMP Free. This polymer displays excellent abrasion resistance with a good balance of hardness and flexibility. Avalure UR 450 is a mixture of PPG-17/IPDI/DMPA copolymer. It has a Brookfield viscosity of about 500–1000 cP, is about 38% solids, and has a pH of about 8 to 10, and is also substantially NMP Free. Avalure UR 450 is a harder version of Avalure UR 445 that displays good gloss, abrasion resistance and flexibility. It forms a tough film with fast property development. As mentioned above, both of these polymers are available from B. F. Goodrich. It is believed that the method of manufacture of these polymers is disclosed in U.S. Pat. No. 6,017,997, which is hereby incorporated by reference in its entirety. The waterproofing agents may be present in an amount of from about 1 percent by weight to about 30 percent by weight, preferably about 6 to about 14 percent by weight.

In other equally preferred embodiments, the waterborne polyurethane polymer can be present in an amount of about 0.1% to about 20% by weight, or in an amount of about 4% to about 7% by weight.

For purposes of the present invention, a "sunscreen active agent" shall include all of those materials which are regarded as acceptable for use as active sunscreening ingredients. Approval by a regulatory agency is generally required for inclusion of active agents in formulations intended for human contact, and those active agents which have been or are currently approved for sunscreen use in the United States include, without limitation, paraminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide and zinc oxide, diethanolamine methoxycinnamate, digalloy trioleate, ethyl dihydroxypropyl PABA, glyceryl aminobenzoate, lawsone with dihydroxy acetone, and red petrolatum. Several other sunscreen active ingredients are accepted for use in other countries. It is typical to use combinations of two or more sunscreen ingredients in a formulation to achieve higher levels of ultraviolet absorption or to provide useful absorption over a wider range of ultraviolet wavelengths than can be the case with a single active component. Preferably, the amount of sunscreen active agent and/or agents are present in an amount that is consistent with the FDA sunscreen monograph for sunscreen active agent and/or agents that are believed to provide the requisite SPF in accordance with the FDA monograph for such sunscreens.

The term "emulsion" shall be used herein to identify oil-in-water (o/w) or water in oil (w/o) type dispersion formulations intended for application to the skin, particularly lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers and the like, depending on the intended uses for the formulations.

The present invention is not dependent upon any particular formulation technique, it being recognized that the choice of specific formulation components may well make necessary some specific formulation procedure.

Suitable emulsifiers for one aspect of the invention are those known in the art for producing oil-in-water type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase, and assists with both the formation and the maintenance, or stability, of the emulsion. Sunscreen products are normally lotions, but creams, gels, solutions, sprayable liquids and other forms are also useful and may be prepared by a proper choice of components.

Particularly preferred emulsifiers are a mixture of cetearyl glucoside and cetearyl alcohol, available under the trade name Emulgade PL68/50 from Henkel KGaA, and PEG 30 dipolyhydroxy stearate, available under the trade name Arlacel 135 from ICI. Also preferred are various $C_{12-15}$, $C_{12-16}$ and $C_{14-15}$ alcohols available from various manufacturers, and Ceteareth 2, 10, 18, 22, Ceteth-1 and 20, cetyl dimethicone copolyol, and cetyl phosphate, glyceryl stearate, Oleth 3 and 10, polyglyceryl 3 methylglucose distearate sorbitan isostearate, steareth 2, 10, and/or 20.

Suitable emulsifiers for another aspect of the invention are those known in the art for producing water-in-oil type emulsions. The typical water-in-oil emulsifier has a HLB value of about 4 to about 6, however, this "rule" is also known to have numerous exceptions.

The formulations of the present invention are waterproof and can serve as sunscreen formulations. The formulations of the present invention prevent the sunscreen active agent from migrating across the skin's surface. This property is especially beneficial for application of the formulation to the face where it is desirable to keep sunscreens from migrating into the eye from the surrounding facial areas. The formulations of the invention also prevent partitioning of the formulation into deeper layers of the stratum corneum, anther beneficial effect of the formulations of the present invention.

Insect repelling components are also a desirable ingredient in sunscreen formulations, since the formulations are normally used primarily by persons engaged in outdoor activities. The most widely used active agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less. The formulations of the present invention are particularly useful as insect repellants because they do not penetrate the skin.

As used herein, an after sun emulsion formulation is defined as a formulation that can be administered after a user has been in the sun for any amount of time and is a formulation that provides a soothing or healing effect that is pleasant to the user. Such a formulation can contain, for instance, aloe vera, vitamins A and E, etc.

The compositions of the present invention may contain a wide range of additional, optional components. The CTFA Cosmetic Ingredient Handbook, Seventh Edition, 1997, and the Eighth Edition, 2000, which are both incorporated by reference herein in their entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, pacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, waterproofing agents, and viscosity increasing agents (aqueous and nonaqueous).

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or composition can range from about 15 percent to 95 weight percent.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or dicaprylyl ether, available under the trade name Cetiol OE also from Henkel KgaA, or a $C_{12}$–$C_{15}$ Alkyl Benzoate sold under the trade name Finsolv TN, available from Finetex. One or more emollients may be present ranging in amounts from about 1 percent to about 10 percent by weight, preferably about 5 percent by weight. Another suitable emollient is DC 200 Fluid 350, a silicone fluid, available from Dow Corning Corp. Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract. Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 percent to about 10 percent by weight, preferably about 5 percent by weight. Other suitable humectants include, inter alia, fructose, glucose, glycerin, lactic acid, PCA, potassium lactate and PCA, propylene glycol, sodium lactate and PCA.

A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc., and/or an epichlorohydrin cross-linked glyceryl starch, available from National Starch under the current tradename of Vulca 90 starch.

It may be advantageous to incorporate thickening agents, such as, for instance, Carbopol Ultrez, or alternatively, Carbopol ETD 2001, available from the B. F. Goodrich Co, Abil Wax 9801, a surfactant available from Gold Schmidt, Alginic Acid, available from Kelco, cellulose gum, available from TIC Gums, ammonium acrylates copolymer, ammonium pollacryloyl dimethyl taurate, bentonite available from Southern Clay, guar hydroxpropyltrimonium chloride available from Henkel, hydroxy propylprocellulose available from Aqualon, magnesium aluminum silicate, available from Salomon, potassium alginate available from Kelco, beeswax available from Strah & Pitsch, and behenyl alcohol available from Nikko.

A waterproofing or water resistance agent is a hydrophobic material that imparts film forming and waterproofing characteristics to an emulsion. A waterproofing agent that can be used in conjunction with the waterproofing agents of the present invention can be a copolymer of vinyl pyrollidone and eicosene and dodecane monomers such as the Ganex V 220 and Ganex V 216 Polymers, respectively, available from ISP Inc. of Wayne, N.J. U.S.A. Still other suitable waterproofing agents include poly alfa olefin polymers, such as Performa V 825 available from New Phase Technologies and polyanhydride resin No. 18 available under the trade name PA-18 from Chevron.

An antimicrobial preservative is a substance or preparation which destroys, or prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may be in the product from growing during manufacturing and distribution of the product and during use by consumers, who may further inadvertently contaminate the products during normal use. Typical preservatives include the lower alkyl esters of parahydroxybenzoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton. One or more antimicrobial preservatives can optionally be included in an amount ranging from about 0.001 to about 10 weight percent, preferably about 0.05 to about 1 percent.

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, Vitamin E and Vitamin C. One or more antioxidants can optionally be included in the sunscreen composition in an amount ranging from about 0.001 to about 5 weight percent, preferably about 0.01 to about 0.5 percent.

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.2 weight percent preferably about 0.01% weight percent.

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

A pH modifier is a compound that will adjust the pH of a formulation to a lower, e.g., more acidic pH value, or to a higher, e.g., more basic pH value. The formulations of the present invention may contain such pH modifiers as is necessary.

The invention will be further described by means of the following examples, which are not intended to limit the invention, as defined by the appended claims, in any manner.

EXAMPLE 1

| Ingredient | Percent W/W |
| --- | --- |
| Part A | |
| Emulgade PL 68/50 | 4 |
| Arlacel P135 | 0.1 |
| Abil Wax 9801 | 2 |
| Homomenthyl Salicylate 3 | 10 |
| Octocrylene | 4 |
| Neoheliopan OS | 5 |
| Parsol 1789 | 2 |
| Part B | |
| USP Purified Water | 61.7 |
| Propylene Glycol USP | 4 |
| Avalure UR-450 | 6 |
| PNC 400 Thickening Agent | 0.2 |
| Part C | |
| Liquapar PE | 1 |

The ingredients of Part A were added to a beaker and heated to 65° C. and mixed until homogenous. In a separate beaker, PNC 400 was added to the water and allowed to hydrate for about 40 minutes. The remaining ingredients of Part B were then added to the beaker, heated to 65° C. and stirred moderately. While stirring, Part A was added to Part B. The batch was cooled while mixing to about 60° C. Thereafter, Part C was added, and the mixture was stirred and allowed to cool to room temperature.

EXAMPLE 2

| Ingredient | Percent W/W |
| --- | --- |
| Part A | |
| Emulgade PL 68/50 | 4 |
| Arlacel P135 | 0.3 |
| Lexol IPL | 5 |
| Abil Wax 9801 | 2 |
| Cetiol OE | 3 |
| Parsol MCX | 7.5 |
| ZnO-USP1-12 | 10 |
| Part B | |
| USP Purified Water | 56.9 |
| Propylene Glycol USP | 4 |
| Avalure UR-450 | 6 |
| PNC Thickening Agent | 0.3 |
| Part C | |
| Liguapar PE | 1 |
| Part D | |
| USP Purified Water | QS |

All of the ingredients, with the exception of zinc oxide of Part A, were added to a beaker and heated to 65° C. while being mixed with a dispersator. Upon reaching homogeneity, zinc oxide was added and dispersed therein. In a separate beaker, the PNC was dispersed in water and allowed to hydrate for about 40 minutes. Then the remaining ingredients of Part B were added and heated to 65° C. with moderate stirring. Thereafter, Part A was added to Part B and the resulting solution was homogenized for about a minute. Thereafter, parts C and D were added. The resulting formulation has an SPF of 28.

EXAMPLE 3

| Ingredient | Percent W/W |
| --- | --- |
| Part A | |
| Lexol IPL | 5 |
| Abil Wax 9801 | 3 |
| Cetiol OE | 3 |
| Parsol MCX or Neoheliopan AV | 7.5 |
| ZnO-USP1-I2 | 10 |
| Part B | |
| USP Purified Water | 58.9 |
| Glycerin, USP, 99% | 3 |
| Avalure UR-450 | 6 |
| Simulgel A | 2.6 |
| Part C | |
| Liquapar PE | 1 |

Add all of the ingredients of Part A, except zinc oxide, in to a beaker and mix with a dispersator. When the oil is homogeneous, disperse ZnO with dispersator. In a separate beaker, combine the ingredients of Part B, except Sepigel 305, and mix completely. Add Sepigel 305 and continue mixing. While stirring add phase A to Phase B until complete. Continue mixing. Add phase C under normal mixing.

EXAMPLE 4

| Ingredient | Percent W/W |
| --- | --- |
| Lexol IPL | 5 |
| Abil Wax 9801 | 3 |
| Cetiol OE | 3 |
| Parsol MCX or Neoheliopan AV | 7.5 |
| ZnO-USP1-I2 | 10 |
| Part B | |
| USP Purified Water | 58.9 |
| Glycerin, USP, 99% | 3 |
| Avalure UR-450 | 6 |
| Sepigel 305 | 2.6 |
| Part C | |
| Liquapar PE | 1 |

Add all of the ingredients of Part A, except the zinc oxide, to a beaker and mix with a dispersator. When the oil is homogeneous, disperse ZnO with dispersator. In a separate beaker, combine the ingredients of Part B, except Sepigel 305 and mix completely. Add the Sepigel 305 and continue mixing. While stirring, add phase A to Phase B until complete. Continue mixing. Add phase C under normal mixing.

EXAMPLE 5

| Ingredient | Percent W/W |
| --- | --- |
| Avalure UR 450 | 13.5 |
| Ethanol | 51.5 |
| SF 1528 | 6 |
| Octocrylene | 10 |
| Oxybenzone | 6 |
| Parsol 1789 | 3 |
| HMS | 10 |

This preparation is a sunscreen loaded gel.

The ability of waterborne polyurethanes to stop sunscreens from migrating across skin's surface was measured using two different methods. One method includes a pre-application of the waterborne polyurethane followed by application of a sunscreen emulsion on top of it. Polymers that show an affinity for the sunscreens are capable of reducing the extent to which sunscreens migrate across skin's surface compared to sunscreen migration on bare skin. The second method involves simultaneous application of polymer with sunscreens within the same emulsion.

Preapplication of Polymer Solution Followed by Sunscreen Application 50 microliters of a solution of the waterborne polyurethane was applied directly to a 5 cm×5 cm area of skin on the inner forearm and allowed to air dry for about 15 minutes. A smaller area of 0.5 cm×5 cm was then marked off diagonally across the polymer-treated site. Within this smaller area on top of the polymer was applied a commercial SPF 45 sunscreen product containing only organic sunscreens at a density of 2 ul/cm$^2$. As a control, the commercial SPF 45 sunscreen was also applied to a 0.5 cm×5.0 cm skin site on the inner aspect of forearm that was not pre-treated with polyurethane polymer (i.e., bare skin).

After application, the rectangular strips of sunscreen were visualized under a Wood's lamp and the width of the sunscreen application was measured (in all cases, the original widths measured between 3–5 mm). The sunscreen-treated sites were then left on the skin for four hours. After four hours, the sites were again viewed under Wood's lamp and the width of the sunscreen application was re-measured. Thus, the extent to which sunscreen migration occurred over a time course of four hours was quantified. The ability of the polymer to reduce or increase sunscreen migration across skin's surface was also determined simply by comparing the extent to which sunscreen migrated on polymer-treated versus untreated skin.

Results showing the ability of two different waterborne polyurethane polymers to prevent organic sunscreens from migrating across skin appear in Table 1. The results display that both of the waterborne polyurethane polymers tested completely prevented organic sunscreens from migrating across skin's surface over a four-hour period. Results indicate that the polyurethane films are preformed on the skin prior to the sunscreen application. This indicates that the films themselves have a chemical affinity for the sunscreen actives that prevents sunscreens from migrating outside their area of application.

TABLE 1

Results showing ability of waterborne polyurethane polymers applied as pre-treatments to prevent sunscreens from migrating across skin's surface.

| Treatment Site | Subject | Migration Width[1] After 4 Hours (mm) |
|---|---|---|
| 10% Avalure UR-450 | 1 | 4 |
| Sunscreen Alone | 1 | 25 |
| 10% Avalure UR-450 | 2 | 3 |
| Sunscreen Alone | 2 | 25 |
| 10% Avalure UR-445 | 3 | 4 |
| Sunscreen Alone | 3 | 24 |
| 10% Avalure UR-445 | 4 | 4 |
| Sunscreen Alone | 4 | 19 |
| 10% Avalure UR-445 | 5 | 3 |
| Sunscreen Alone | 5 | 18 |

[1]The width of the sunscreen product to skin immediately after application was typically 3 to 4 mm.

EXAMPLE 6

Simultaneous Application of Waterborne Polyurethane Polymers With Organic Sunscreens Waterborne polyurethane polymers were incorporated directly into an emulsion along with organic sunscreens. In this case, sunscreen migration of emulsions containing Avalure UR-450 polyurethane was compared to an emulsion that did not contain Avalure UR-450.

As in Example 3, 0.5 cm×5.0 cm strips of sunscreen lotion were applied to inner forearms of volunteers. The width of the applications was measured immediately after application and after four hours.

The results appear in Table 2. The results indicate that waterborne polyurethane polymers prevent the organic sunscreens from migrating across skin's surface. Thus, it appears that the waterborne polyurethane polymers are as effective in stopping sunscreen migration when they are incorporated directly into an emulsion as they are when they are applied prior to a sunscreen product.

TABLE 2

Results showing ability of waterborne polyurethane polymers to reduce sunscreen when incorporated into emulsions with sunscreens.

| Treatment Site | Subject | Migration Width[1] After 4 Hours (mm) |
|---|---|---|
| Formula with Polyurethane | 1 | 4 |
| Formula without Polyurethane | 1 | 14 |
| Formula with Polyurethane | 2 | 6 |
| Formula without Polyurethane | 2 | 13 |
| Formula with Polyurethane | 3 | 6 |
| Formula without Polyurethane | 3 | 13 |
| Formula with Polyurethane | 4 | 5 |
| Formula without Polyurethane | 4 | 18 |

[1]The width of the sunscreen product to skin immediately after application was typically 3 to 4 mm.

The results confirm the ability of waterborne polyurethane polymers to prevent organic sunscreens from migrating across the skin's surface. This has relevance especially for application of products to face where it is desirable to keep sunscreens from migrating into the eye from surrounding areas and causing eye stinging.

EXAMPLE 7

Demonstration of Waterborne Polyurethane Polymers to Retard Penetration of Sunscreens into Skin After application of conventional sunscreen emulsions to skin, organic sunscreen agents begin to partition into the stratum corneum, the outer most layer of skin. The extent that sunscreen agents partition into the stratum corneum can be quantitiated by tape-stripping skin after sunscreen application at defined time points. The ability of excipients to retard sunscreen penetration into skin can then be investigated by comparing extents of partitioning in the presence or absence of specific ingredients that may retard partitioning.

Sunscreen products were applied to skin in the absence and presence of polymers according to Examples 6 and 7 above. At defined time points, the sunscreen treated sites were tape-stripped six consecutive times using 3M Highland Invisible Tape. The tape was 1.9 cm wide or about five times the width the sunscreen application. Each tape strip was placed separately in a 25 ml scintillation vial and left to soak overnight in isopropyl alcohol. After soaking overnight, an aliquot of the isopropyl alcohol was removed and the sunscreen level measured using a Perkin-Elmer UV-Vis Spectrophotometer. The amount of sunscreen recovered from each tape strip was calculated and then the levels determined from each of the six tape strips were summed to calculate the total amount of sunscreen recovered from the skin at each defined time point.

Mean recoveries of sunscreen from skin tape-stripped either immediately or after four hours appear in Table 3. Each value represents a mean from four different individuals.

TABLE 3

Mean percent recoveries of sunscreens from skin in the absence and presence of polymers as a function of time following product application.

| Polymer Treatment | Immediate Tape-Strip (%) | 4 Hour Tape-Strip (%) |
|---|---|---|
| None | 101 ± 5 | 31 ± 6 |
| 10% Avalure UR-450 (Example 3) | ND[1] | 66 ± 19 |
| 10% Avalure UR-445 (Example 3) | ND | 80 ± 13 |
| Avalure UR-450 (N14-052) (Example 4) | ND | 83 ± 19 |

[1]ND = Not determined for polymer treatments.

The extent to which a typical SPF 45 sunscreen product partitions into the stratum corneun as a function of time was determined by tape-stripping sunscreen-treated skin immediately and after four hours. The results show that after a residence time of four hours on skin, the levels of sunscreens that can be recovered from the skin falls significantly. About 70% of the applied sunscreen load partitioned deeper into the stratum corneum than could be recovered from six consecutive tape strips.

The ability of waterborne polyurethanes to prevent or retard sunscreens from partitioning into deeper layers of stratum corneum is demonstrated by the data in Table 3. Pre-treating skin with either Avalure UR-450 or Avalure UR-445 as in Example 6 increased the levels of sunscreens recovered from skin by at least a factor of two. Retardation of sunscreen partitioning was about as effective when Avalure UR-450 was incorporated directly into an emulsion with sunscreens as opposed to being applied as a pretreatment.

What is claimed is:

1. A sunscreen formulation for topical application, the formulation comprising a waterborne polyurethane polymer, a thickening agent, a humectant, an emulsifying agent, and at least one sunscreen active agent.

2. The formulation of claim 1, wherein the formulation is an oil-in-water emulsion.

3. The formulation of claim 1, wherein the formulation is a water-in-oil emulsion.

4. The formulation of claim 1, wherein the sunscreen active agent is organic.

5. The formulation of claim 1, wherein the sunscreen active agent is inorganic.

6. The formulation of claim 1, wherein there is at least two sunscreen active agents.

7. The formulation of claim 6, wherein the at least two sunscreen active agents are a mixture of organic and inorganic sunscreen active agents.

8. The formulation of claim 1 further comprising an emollient.

9. The formulation of claim 1, wherein the waterborne polyurethane polymer is present in an amount of about 0.1% to about 20% by weight.

10. The formulation of claim 9, wherein the waterborne polyurethane polymer is present in an amount of about 4% to about 7% by weight.

11. An oil-in-water emulsion formulation, the formulation comprising a nonaqueous phase, an aqueous phase, an oil-in-water emulsifying agent, a waterborne polyurethane polymer, a humectant, a thickening agent, and at least one sunscreen active agent.

12. The emulsion formulation of claim 11, wherein the sunscreen active agent is inorganic.

13. The emulsion formulation of claim 11, wherein the sunscreen active agent is an organic compound.

14. The emulsion formulation of claim 11 wherein there are at least two sunscreen active agents.

15. The emulsion formulation of claim 14, wherein the at least two sunscreen active agents are a mixture of two organic and inorganic sunscreen active agents.

16. The formulation of claim 11, wherein the waterborne polyurethane polymer is present in an amount of about 0.1% to about 20% by weight.

17. The formulation of claim 16, wherein the waterborne polyurethane polymer is present in an amount of about 4% to about 7% by weight.

18. The formulation of claim 1, wherein the waterborne polyurethane polymer is present in an amount of about 1% to about 30% by weight.

19. The formulation of claim 1, wherein the waterborne polyurethane polymer is present in an amount of about 6 to about 14% by weight.

20. The formulation of claim 11, wherein the waterborne polyurethane polymer is present in an amount of about 1% to about 30% by weight.

21. The formulation of claim 11, wherein the waterborne polyurethane polymer is present in an amount of about 6 to about 14% by weight.

* * * * *